United States Patent
Yamamura et al.

(10) Patent No.: US 10,836,694 B2
(45) Date of Patent: Nov. 17, 2020

(54) METHOD FOR PRODUCING HIGH CONCENTRATION ALCOHOL

(71) Applicant: Mitsubishi Chemical Corporation, Chiyoda-ku (JP)

(72) Inventors: Tadafumi Yamamura, Chiyoda-ku (JP); Hideto Hidaka, Chiyoda-ku (JP); Hiroyuki Kakiuchi, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/525,085

(22) Filed: Jul. 29, 2019

(65) Prior Publication Data

US 2019/0352244 A1 Nov. 21, 2019

Related U.S. Application Data

(63) Continuation of application No. PCT/JP2018/002682, filed on Jan. 29, 2018.

(30) Foreign Application Priority Data

| Jan. 30, 2017 | (JP) | 2017-014206 |
| Jun. 13, 2017 | (JP) | 2017-115962 |
| Sep. 25, 2017 | (JP) | 2017-183629 |

(51) Int. Cl.
*C07C 29/80* (2006.01)
*B01D 3/00* (2006.01)
(Continued)

(52) U.S. Cl.
CPC .............. *C07C 29/80* (2013.01); *B01D 3/005* (2013.01); *B01D 3/145* (2013.01);
(Continued)

(58) Field of Classification Search
CPC ......... C07C 29/76; C07C 29/80; B01D 3/005; B01D 3/145; B01D 17/0202; B01D 71/028
See application file for complete search history.

(56) References Cited

U.S. PATENT DOCUMENTS

2017/0204030 A1* 7/2017 Maeda .................... C07C 29/76

FOREIGN PATENT DOCUMENTS

| JP | 2000-334257 A | 12/2000 |
| JP | 2006-263561 A | 10/2006 |

(Continued)

OTHER PUBLICATIONS

Extended European Search Report dated Jan. 15, 2020, in Patent Application No. 18745139.8, 7 pages.
(Continued)

*Primary Examiner* — Yate' K Cutliff
(74) *Attorney, Agent, or Firm* — Oblon, McClelland, Maier & Neustadt, L.L.P.

(57) ABSTRACT

The present invention aims to improve the production capacity of alcohol in a method of producing high concentration alcohol using a distillation column and an adsorption-desorption column. The method is a method of producing high concentration alcohol by dehydration of a water-alcohol mixture, including: a distillation step of introducing a water-alcohol mixture into a distillation column to obtain crude alcohol; and an adsorption-desorption step of introducing a part of the crude alcohol into an adsorption-desorption column to obtain high concentration alcohol; wherein a further part of the crude alcohol is introduced into a dehydration apparatus to obtain high concentration alcohol.

19 Claims, 15 Drawing Sheets

(51) Int. Cl.
  *B01D 3/14* (2006.01)
  *B01D 17/02* (2006.01)
  *B01D 71/02* (2006.01)
  *C07C 29/76* (2006.01)
(52) U.S. Cl.
  CPC ....... *B01D 17/0202* (2013.01); *B01D 71/028* (2013.01); *C07C 29/76* (2013.01)

(56) References Cited

FOREIGN PATENT DOCUMENTS

| JP | 2008-86988 A | 4/2008 |
|---|---|---|
| JP | 2014-118377 A | 6/2014 |
| WO | WO 2016/067677 A1 | 5/2016 |

OTHER PUBLICATIONS

International Preliminary Report on Patentability dated Aug. 8, 2019 in PCT/JP2018/002682 (submitting English translation only).

International Search Report dated May 1, 2018 in PCT/JP2018/002682 filed Jan. 29, 2018.

Wojciech Kujawski, et al., "Bioethanol—One of the Renewable Energy Sources", Environment Protection Engineering, vol. 32, No. 1, 2006, pp. 143-149.

Jun-Seong Jeong, et al., "Production of dehydrated fuel ethanol by pressure swing adsorption process in the pilot plant", The Korean Journal of Chemical Engineering, vol. 26, No. 5, 2009, pp. 1308-1312.

Jun-Seong Jeong, et al., "Production of anhydrous ethanol using various PSA (Pressure Swing Adsorption) processes in pilot plant", Renewable Energy, vol. 42, 2012, pp. 41-45.

Kazahiro Okabe, et al., "Energy and Cost Evaluation for the Concentration and Dehydration Process of Bioethanol by Zeolite Membranes", Kagaku Kogaku Ronbunshu, vol. 36, No. 5, 2010, pp. 486-493 (with English abstract and machine translation of "Introduction" part).

Kiminori Sato, et al., "Concentration and Dehydration of Biomass Ethanol", Membrane, vol. 31, No. 1, 2006, pp. 20-21 (with English abstract and machine translation of full text).

* cited by examiner

METHOD FOR PRODUCING HIGH CONCENTRATION ALCOHOL

CROSS-REFERENCE TO RELATED APPLICATION

This is a continuation of International Application No. PCT/JP2018/002682, filed on Jan. 29, 2018, and designated the U.S., and claims priority from Japanese Patent Application No. 2017-014206 which was filed on Jan. 30, 2017, Japanese Patent Application No. 2017-115962 which was filed on Jun. 13, 2017, and Japanese Patent Application No. 2017-183629 which was filed on Sep. 25, 2017, the entire contents of which are incorporated herein by reference.

TECHNICAL FIELD

The present invention relates to a method of producing an alcohol such as ethanol at high concentration, more specifically, a method of producing high concentration alcohol including a distillation step, adsorption-desorption step, and membrane separation step, wherein energy consumption in the whole process is reduced as much as possible to enable efficient production of high concentration alcohol.

BACKGROUND ART

Removal of water alone from a mixture of water and an organic compound such as an alcohol, ketone, or ether is difficult since the mixture of water and the organic compound is an azeotrope having the lowest boiling point, and therefore purification of the organic compound with high purity is difficult by ordinary rectification alone.

Therefore, as a method of removing an organic compound alone with high purity from a mixture of the organic compound and water, a method in which most part of the water is removed by distillation followed by removal of the remaining water with a pressure swing adsorption apparatus (hereinafter also simply referred to as PSA) using an adsorption-desorption column has been proposed (see Patent Literature 1).

As a method of dehydration from a mixture of an organic compound and water without using a large-scale apparatus, a method in which membrane separation means is employed between a distillation column and a PSA has been proposed. A method in which a purge gas discharged from a PSA is supplied to membrane separation means to obtain an organic compound with high purity has also been proposed (see Patent Literature 2).

A method of producing an organic compound, which method is highly efficient as the whole process, wherein a water-organic compound mixture containing water, desorbed from a PSA is supplied to a membrane separation apparatus having a particular zeolite membrane, has also been disclosed (see Patent Literature 3).

PRIOR ART REFERENCES

Patent Literatures

[Patent Literature 1] Japanese Patent Laid-Open No. 2000-334257

[Patent Literature 2] Japanese Patent Laid-Open No. 2008-86988

[Patent Literature 3] Japanese Patent Laid-Open No. 2014-118377

SUMMARY OF THE INVENTION

Problems to be Solved by the Invention

However, when already operating production equipment of high concentration alcohol composed of a distillation column and a PSA is combined with a membrane separation apparatus downstream of the PSA, and a desorbed liquid from the PSA is dehydrated using the membrane separation apparatus to increase the production capacity, the throughput of the PSA is insufficient, and becomes a rate limiting factor even if the distillation column has an enough processing capacity, so that the production capacity cannot be increased, which is problematic.

There has also been a problem that use of the PSA and the membrane separation apparatus in addition to the distillation column leads to a high operating cost.

Means for Solving the Problems

As a result of intensive study, the present inventors discovered that the above problem can be solved by appropriately designing combination of a distillation step using a distillation column, an adsorption-desorption step using an adsorption-desorption column, and a membrane separation step using a membrane separation apparatus, thereby reaching the present invention.

The present invention includes a method of producing high concentration alcohol by dehydration of a water-alcohol mixture, including:

a distillation step of introducing a water-alcohol mixture into a distillation column to obtain crude alcohol; and an adsorption-desorption step of introducing a part of the crude alcohol into an adsorption-desorption column to obtain high concentration alcohol;

wherein a further part of the crude alcohol is introduced into a dehydration apparatus to obtain high concentration alcohol.

Another aspect of the present invention includes a method of producing high concentration alcohol by dehydration of a water-alcohol mixture, including:

a distillation step of introducing a water-alcohol mixture into a distillation column to obtain crude alcohol; and an adsorption-desorption step of introducing the resulting crude alcohol into an adsorption-desorption column to obtain high concentration alcohol 1;

wherein a desorbed liquid discharged from the adsorption-desorption column in the adsorption-desorption step is introduced into a dehydration apparatus 1, and aqueous alcohol obtained from the dehydration apparatus 1 is further introduced into a dehydration apparatus 2, which is a further dehydration apparatus, to obtain high concentration alcohol 2.

Effect of the Invention

According to the present invention, by appropriately designing combination of the distillation step, the adsorption-desorption step, and the membrane separation step, the energy load in each step of the production process of high concentration alcohol can be minimized to reduce energy consumption in the whole process, thereby enabling achievement of enhanced productivity of high concentration alcohol.

Moreover, since a variety of kinds of separation membranes can be used in the membrane separation step, the initial cost for providing the membrane separation step can be reduced.

Moreover, the production capacity of the equipment can be increased even in cases where the adsorption-desorption column (PSA) has an insufficient processing capacity and acts as a rate limiting factor while the distillation column has a sufficient processing capacity.

MODE FOR CARRYING OUT THE INVENTION

Figure 1:
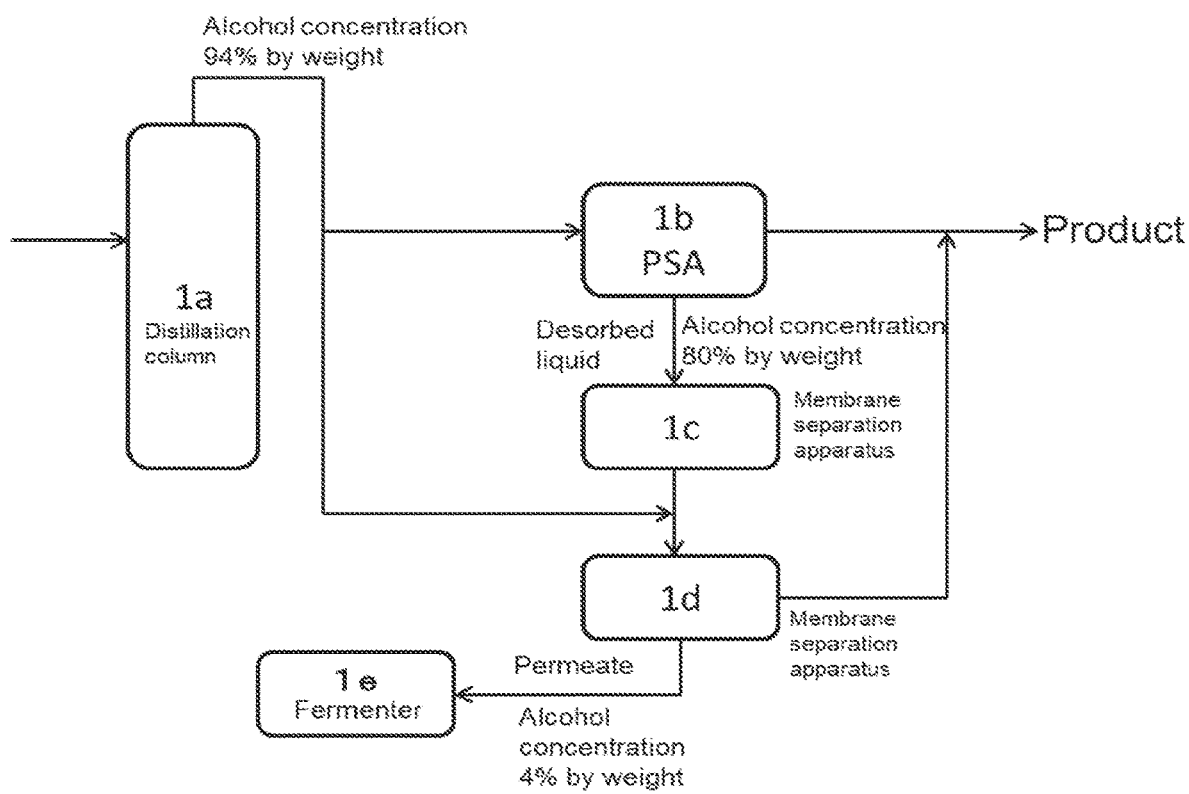
FIG. 1 is a process flow diagram showing an example of the method of producing high concentration alcohol of the present invention.

The constituents described below are merely examples of embodiments (representative examples) of the present invention, and the present invention is not limited thereto.

The present invention relates to a method of producing high concentration alcohol by dehydration of a water-alcohol mixture, including:

a distillation step of introducing a water-alcohol mixture into a distillation column to obtain crude alcohol; and an adsorption-desorption step of introducing a part of the crude alcohol into an adsorption-desorption column to obtain high concentration alcohol;

wherein a further part of the crude alcohol is introduced into a dehydration apparatus to obtain high concentration alcohol.

Preferred examples of the high concentration alcohol to be produced include lower alcohols that are industrially mass-produced, such as alcohols having about 1 to 5 carbon atoms, more specifically, methanol, ethanol, butanol, and their mixtures. The method is especially preferably used for production of ethanol or butanol. In particular, the method is preferred for ethanol or butanol produced by alcohol fermentation using a biomaterial. The method is especially preferably used for ethanol produced by alcohol fermentation.

The present invention is described below using as an example a production method of ethanol produced by alcohol fermentation using a biomaterial. However, the scope of the present invention is not limited thereto.

(Fermentation Step)

In cases where a biomaterial is used in the present embodiment, the method usually includes a fermentation step of fermenting a material to obtain a water-ethanol mixture containing ethanol at not more than 20% by weight.

Examples of the material to be used in the fermentation step include carbohydrate materials such as sugar cane, sugar beet, and molasses and the like using these as materials; tubers such as sweet potato and potato; starchy materials such as cereals including maize, wheat, and rice; and fibrous materials such as celluloses, waste papers, and building wastes.

Among these materials, carbohydrate materials can be applied as they are to the fermentation step. However, starchy materials and fibrous materials need a pretreatment step by pulverization, liquefaction, saccharification, and/or the like. Thus, depending on the type of the material, the pretreatment step may be required prior to the fermentation step. The pretreatment step may be carried out as appropriate depending on the material, and known methods may be applied thereto.

The fermentation step is a step in which alcohol fermentation of a material is carried out by a microorganism such as a fermentative microorganism. A water-alcohol mixture is obtained by the alcohol fermentation.

The fermentative microorganism is not limited as long as it is a microorganism capable of alcohol fermentation using as a carbon source at least one of glucose, glucose dimer, and glucose polymer. Examples of the microorganism include yeast and *Zymomonas*.

The alcohol concentration in the water-alcohol mixture obtained by the alcohol fermentation in the fermenter in the fermentation step is usually not less than 1% by weight, and usually not more than 20% by weight or not more than 15% by weight. The alcohol concentration is increased through the later-described distillation step and/or the like.

(Distillation Step)

The water-alcohol mixture obtained by the fermentation step is usually introduced into the distillation step. In the distillation step, alcohol is usually concentrated using distillation columns of two or more stages. The distillation columns may include a preliminary distillation column such as a mash column, or a rectifying column. The number of stages of the distillation columns is not limited to two. In cases where the alcohol concentration in the water-alcohol mixture obtained by the fermentation step is low, the water-alcohol mixture may be supplied to a preliminary distillation column to increase the alcohol concentration, and the number of stages of the distillation columns is preferably two or three.

From the viewpoint of reducing the energy consumption, it is preferred to perform the concentration in the preliminary distillation column to an alcohol concentration of usually not less than 30% by weight, preferably not less than 35% by weight, more preferably not less than 40% by weight, still more preferably not less than 45% by weight. There is no upper limit of the alcohol concentration. The alcohol concentration is usually less than 70% by weight, preferably not more than 65% by weight, more preferably not more than 60% by weight, still more preferably not more than 55% by weight. In cases where the alcohol concentration is within the range described above, reflux is rarely required, and the amount of water to be evaporated can be small, which is preferred.

When necessary, for example, before supplying the mixture into the preliminary distillation column, after distillation of the mixture in the preliminary distillation column, or before supplying the mixture to the rectifying column, filtration such as microfiltration, ultrafiltration, and/or nanofiltration for removal of insoluble substances, and/or macromolecular components in the solution; and/or neutralization; may be carried out individually or in combination.

The water-alcohol mixture concentrated in the preliminary distillation column is then introduced into the rectifying column to increase the alcohol concentration. The distillate after the rectification in the rectifying column, for example, the overhead distillate (crude alcohol), has an alcohol concentration of usually not less than 30% by weight, preferably not less than 50% by weight, more preferably not less than 80% by weight, especially preferably not less than 85% by weight, and usually not more than 98% by weight, preferably not more than 95% by weight, more preferably not more than 94% by weight, especially preferably not more than 90% by weight.

When the alcohol concentration is not more than the upper limit, the load on the distillation column and the like tends to be reduced to improve the energy efficiency of the whole process. When the alcohol concentration is not less than the lower limit, the water concentration is not too high; the amount of the adsorbent packed in the later-mentioned adsorption-desorption column does not need to be increased; and a possible increase in the equipment cost due to an increased size of the adsorption-desorption column equipment can be avoided. Thus, the frequency of regeneration of the adsorbent can be reduced, and the operating cost tends to be suppressed.

The rectifying column may have a side stripper. By having the side stripper, the water-alcohol mixture can be drawn from one or several sites in a stage(s) in the middle of the distillation columns to achieve the rectification.

The above description for the distillation step is for a case where a preliminary distillation column and a rectifying column are used as distillation columns. The distillation columns may be of a single stage, two stages, or not less than three stages.

In such a manner, in the distillation step, a water-alcohol mixture containing alcohol at not more than 20% by weight is introduced into the distillation column to obtain crude alcohol containing alcohol usually at not less than 30% by weight.

(Adsorption-Desorption Step)

In the adsorption-desorption step, the crude alcohol obtained by the distillation step is introduced into an adsorption-desorption column to perform dehydration, to obtain high concentration alcohol containing alcohol usually at not less than 98% by weight.

One characteristic of the present embodiment is that a part of the crude alcohol obtained by the distillation step is introduced into the adsorption-desorption column.

The adsorption-desorption column used in the adsorption-desorption step may be any of a column based on pressure swing adsorption (PSA), a column based on temperature swing adsorption (TSA), and a column based on pressure-temperature swing adsorption (PTSA), which has their combination.

PSA has a function to allow adsorption of water and the like to an adsorbent when the pressure is increased, and to allow desorption of the water and the like from the adsorbent when the pressure is decreased. On the other hand, TSA has a function to allow adsorption of water and the like to an adsorbent, and to allow desorption of the water and the like from the adsorbent when a heating gas (for example, nitrogen) is supplied to increase the temperature.

PSA, TSA, and PTSA are widely used since they have relatively simple apparatus configurations. Examples of the adsorbent include powders and pellets of zeolites such as LTA-type zeolite and FAU-type zeolite. Synthetic zeolites such as "Molecular Sieve" (trade names) are preferably used because of their high dehydration capacities.

The crude alcohol to be introduced into the adsorption-desorption column has an alcohol concentration of usually not less than 30% by weight, preferably not less than 50% by weight, more preferably not less than 80% by weight, still more preferably not less than 85% by weight, and usually not more than 98% by weight, preferably not more than 95% by weight, more preferably not more than 94% by weight, still more preferably not more than 90% by weight.

When the alcohol concentration is not more than the upper limit, the load on the distillation column and the like tends to be reduced, and the total energy efficiency tends to be improved. When the alcohol concentration is not less than the lower limit, the water concentration is not too high; the amount of the packed adsorbent does not need to be increased; and a possible increase in the equipment cost due to an increased size of the adsorption equipment can be avoided. Thus, the frequency of regeneration of the adsorbent in the adsorption apparatus can be reduced, and the operating cost tends to be suppressed.

In the adsorption-desorption column, from the crude alcohol introduced into the adsorption-desorption column, water is adsorbed to the adsorbent, and the unadsorbed alcohol component is obtained as high concentration alcohol.

The high concentration alcohol obtained here has an alcohol concentration of usually not less than 98% by weight, preferably not less than 98.9% by weight, more preferably not less than 99.5% by weight, and usually not more than 100% by weight.

On the other hand, the water adsorbed to the adsorbent usually contains a small amount of alcohol. The water containing a small amount of alcohol is desorbed from the adsorbent. The desorption is usually carried out by introducing a high concentration of alcohol to the adsorbent that is in a state where the water is contained. The high concentration of alcohol to be used for the desorption has an alcohol concentration of usually not less than 98% by weight, preferably not less than 98.9% by weight, more preferably not less than 99.5% by weight, and usually not more than 100% by weight. The high concentration of alcohol to be used for the desorption may be the high concentration alcohol obtained by the introduction into the adsorption-desorption column.

After the desorption, a mixed liquid of the alcohol-containing water contained in the adsorbent and the high concentration of alcohol used for the desorption is obtained. In the present description, this is called the desorbed liquid obtained by the adsorption-desorption step. The desorbed liquid may have an alcohol concentration of usually 30% by weight to 80% by weight, more preferably 40% by weight to 70% by weight.

Although the desorbed liquid is preferably introduced into the later-mentioned dehydration apparatus A or dehydration apparatus B, the desorbed liquid may be returned to the distillation step to concentrate alcohol again in the distillation column.

The adsorption-desorption step is usually carried out by a method using two or more adsorption-desorption columns, wherein the adsorption is carried out with one of the columns, and the desorption is carried out with a further column, while the adsorption and the desorption are repeated using these columns alternately.

(Dehydration Step)

One characteristic of the present embodiment is that a part of the crude alcohol obtained by the distillation step is introduced into an adsorption-desorption column, and that a further part is introduced into a dehydration apparatus. By this, in the process of production of high concentration alcohol, the load on the adsorption-desorption column such as PSA, which consumes the largest amount of energy, can be reduced, and therefore the energy consumption can be reduced. The process of dehydration by the dehydration apparatus is also referred to as the dehydration step.

Here, preferably not less than 50% by weight, more preferably not less than 60% by weight, still more preferably not less than 70% by weight, and preferably not more than 90% by weight, more preferably not more than 80% by weight of the crude alcohol obtained by the distillation step is preferably introduced into the adsorption-desorption column. Preferably not less than 10% by weight, more preferably not less than 20% by weight, and preferably not more than 40% by weight, more preferably not more than 30% by weight of the crude alcohol is preferably introduced into the dehydration apparatus.

By the introduction of the part of the crude alcohol into the dehydration apparatus, the crude alcohol can be dehydrated, and high concentration alcohol of usually not less than 98% by weight, similar to the one described above, can be obtained here again.

The permeate (separated water, which may contain alcohol) from the dehydration apparatus and the desorbed liquid (which may contain alcohol) from the adsorption-desorption column may be returned to an earlier step such as the fermenter.

The high concentration alcohol dehydrated by the dehydration apparatus may be further introduced into a further dehydration apparatus.

In the introduction of the part of the crude alcohol obtained by the distillation step into the dehydration apparatus (which may be hereinafter referred to as dehydration apparatus A), this part of the crude alcohol may be mixed with the desorbed liquid obtained from the adsorption-desorption column, and the resulting mixture may be introduced into the dehydration apparatus. In cases where alcohol is further recovered from the desorbed liquid, and introduced as it is into the dehydration apparatus, the energy load on the dehydration apparatus may be increased since the desorbed liquid has a low alcohol concentration. Here, by mixing the part of the crude alcohol with the desorbed liquid, a mixed liquid having an increased alcohol concentration can be obtained. By introducing this mixed liquid into the dehydration apparatus, the energy load on the dehydration apparatus can be reduced. In particular, in cases where a membrane separation apparatus is used as the dehydration apparatus, only particular membranes having water resistance (for example, CHA-type zeolite membranes) can be used when the alcohol concentration is low, and the water content is high. However, for the liquid having an increased alcohol concentration, a broader range of zeolite membranes can be selected and used.

Since the desorbed liquid often has a very low alcohol concentration, the desorbed liquid may be introduced into a further dehydration apparatus (which may be hereinafter referred to as dehydration apparatus B), for example, a membrane separation apparatus or a distillation column such as a stripper, to increase the alcohol concentration before the mixing with the part of the crude alcohol. In this process, the alcohol concentration of the liquid obtained from the dehydration apparatus B before the mixing with the part of the crude alcohol (which may be hereinafter referred to as liquid A) is preferably not less than 30% by weight, more preferably not less than 40% by weight, and preferably not more than 80% by weight, more preferably not more than 70% by weight.

The alcohol concentration of the aqueous alcohol is preferably within the range of ±40% by weight, more preferably within the range of ±20% by weight with respect to, especially preferably the same concentration as, the concentration of the crude alcohol obtained from the distillation column.

The mixed liquid prepared by mixing the desorbed liquid from the adsorption-desorption column or liquid A with the part of the crude alcohol, which is to be introduced into the dehydration apparatus A, has an alcohol concentration of preferably not less than 50% by weight, more preferably not less than 70% by weight, and preferably not more than 94% by weight, more preferably not more than 85% by weight.

In cases where two or more lines of distillation steps are included (for example, in cases where a distillation step A and a distillation step B are included), when the desorbed liquid from the adsorption-desorption column or liquid A, and a part of the crude-alcohol-containing liquid obtained from the plurality of distillation steps are introduced together into the dehydration apparatus A, the liquid to be introduced into the dehydration apparatus A has an alcohol concentration of preferably not less than 50% by weight, more preferably not less than 70% by weight, and preferably not more than 94% by weight, more preferably not more than 85% by weight.

The permeate (separated water, which may contain alcohol) after the dehydration by the dehydration apparatus A and the desorbed liquid (which may contain alcohol) may be introduced into the dehydration apparatus B to perform further dehydration.

Similarly, even in cases where, for example, the part of the crude alcohol is not introduced into the dehydration apparatus, the load on the dehydration apparatus can be reduced by utilization of the crude alcohol obtained from the distillation step B.

Two or more dehydration apparatuses may be used as described below with reference to FIG. 8.

The dehydration apparatus herein is not limited as long as it is an apparatus having a dehydration function. The apparatus may be a distillation column such as a rectifying column; a membrane separation apparatus having an inorganic membrane such as a polymer membrane or a zeolite membrane; or an adsorption-desorption column. Also from the viewpoint of energy consumption, a distillation column or a membrane separation apparatus is especially preferably used as the dehydration apparatus. A membrane separation apparatus is more preferred.

The membrane separation apparatus is described below.

(Membrane Separation Apparatus)

The membrane separation apparatus contains a dehydration membrane such as a polymer membrane or an inorganic membrane. With the dehydration membrane, water is separated from alcohol. As the membrane separation method, the pervaporation (PV) method or the vapor permeation (VP) method is employed. From the viewpoint of energy efficiency, the pervaporation (PV) method is preferably employed.

In the PV method, a liquid is brought into contact with a separation membrane, and water is allowed to permeate therethrough. This method is also called the permeation evaporation method or the osmotic evaporation method. In this method, the mixture (supplied liquid) is evaporated through the separation membrane while allowing permeation of only water. By this, alcohol is separated and concentrated. Since cooling of the supplied liquid occurs due to heat of vaporization, the method requires heating means for supplementing it.

In either method, the temperature of the crude alcohol to be introduced is preferably high from the viewpoint of increasing the separation efficiency. The temperature of the crude alcohol to be introduced into the membrane separation apparatus is within the range of preferably 100° C. to 145° C., more preferably 125° C. to 135° C.

The permeation flux of water in the membrane separation apparatus at an ethanol concentration of 95% by weight (PV method; liquid temperature, 100° C.) is preferably not less than 0.1 kg/(m$^2$·h), more preferably not less than 2.0 kg/(m$^2$·h), still more preferably not less than 5.0 kg/(m$^2$·h). In cases where the permeation flux of water is within the range described above, the production efficiency can be increased when the product is directly obtained from the membrane separation apparatus, or the energy efficiency of the adsorption apparatus can be increased when the product is returned from the membrane separation apparatus to the adsorption apparatus. In cases where the value of the permeation flux is high, the membrane separation apparatus can be designed such that the separation membrane area is reduced while a desired concentration volume and a desired concentration rate are maintained, so that compaction of the apparatus is possible.

The membrane separation apparatus may be an apparatus using a single-stage module, or an apparatus using multistage modules that are arranged linearly, in parallel, or in a mode combining these modes. In cases where multistage modules are used, a module(s) using a polymer membrane(s) may be used in combination with a module(s) using a zeolite membrane(s). A plurality of kinds of zeolite membranes may be used in combination. For example, the LTA-type zeolite membrane described below in detail may be used for one module, and a CHA-type zeolite membrane may be used for another module.

The alcohol obtained by introducing the crude alcohol to the membrane separation apparatus may be used as it is as a product in cases where the concentration is sufficiently high (high concentration alcohol). The alcohol obtained may also be returned to the adsorption-desorption step or the dehydration step in cases where the concentration is not sufficiently high.

The alcohol concentration of the high concentration alcohol (product) in the present embodiment is usually not less than 98% by weight, preferably not less than 98.9% by weight, more preferably not less than 99.5% by weight, and usually not more than 100% by weight.

The membrane separation apparatus is not limited as long as it has a dehydration membrane. The dehydration membrane is usually a dehydration membrane having a dehydration function, and examples of such a membrane include polymer membranes such as polyimide membranes, and zeolite membranes. The shape of the membrane is also not limited, and may be any of a planar shape, tubular shape, honeycomb shape, monolith shape, and hollow-fiber shape.

A zeolite membrane as one example of the dehydration membrane is described below in detail.

As the zeolite membrane, a porous support-zeolite membrane complex (hereinafter referred to as zeolite membrane complex), wherein the zeolite membrane is formed on a porous support, is preferably used.

The porous support is preferably an inorganic porous support, and examples of such a support include ceramic sintered bodies of silica, α-alumina, γ-alumina, mullite, zirconia, titania, yttria, silicon nitride, silicon carbide, or the like; sintered metals of iron, bronze, stainless steel, or the like; glasses; and carbon molded bodies. Examples of the inorganic porous support include ceramic sintered bodies containing silica, alumina such as α-alumina or γ-alumina, mullite, zirconia, titania, yttria, silicon nitride, silicon carbide, or the like (ceramic support). Alumina or mullite is preferred.

Since the zeolite membrane complex has the support, it can have higher mechanical strength, and can be easily handled, so that a wide variety of apparatus designs are possible. Moreover, in cases where an inorganic porous support is used, the complex can have excellent heat resistance and chemical resistance since the support is constituted by an inorganic substance.

The shape of the porous support is not limited as long as effective separation is possible for a mixture of liquids or gases. Specific examples of the shape include planar shapes; tubular shapes; honeycomb shapes having a large number of cylindrical, columnar, or rectangular-column pores; and monolith shapes. The porous support may have any of these shapes.

The porous support preferably has zeolite crystallized on its surface (hereinafter also referred to as "porous support surface").

The average pore size of the porous support surface is not limited. The pore size is preferably controlled within the range of usually not less than 0.02 μm, preferably not less than 0.05 μm, more preferably not less than 0.1 μm, especially preferably not less than 0.5 μm, and usually not more than 20 μm, preferably not more than 10 μm, more preferably not more than 5 μm.

In cases where the average pore size is too small, the permeation volume tends to be small, while in cases where the average pore size is too large, the support itself may have insufficient strength, and an increased ratio of pores on the support surface may cause difficulty in formation of a dense zeolite membrane.

The average thickness (wall thickness) of the porous support is usually not less than 0.1 mm, preferably not less than 0.3 mm, more preferably not less than 0.5 mm, especially preferably not less than 0.7 mm, and usually not more than 7 mm, preferably not more than 5 mm, more preferably not more than 3 mm.

The support is used for the purpose of giving mechanical strength to the zeolite membrane. In cases where the average thickness of the support is too small, the porous support-zeolite membrane complex does not have sufficient strength, so that there tends to be a practical problem caused by weakness of the porous support-zeolite membrane complex against impact, vibration, and/or the like. In cases where the average thickness of the support is too large, the permeation flux tends to be low because of poor diffusion of permeated substances.

In cases where the porous support is a cylindrical tube, the outer diameter of the cylindrical tube is usually not less than 3 mm, preferably not less than 5.5 mm, more preferably not less than 9.5 mm, especially preferably not less than 11 mm, and usually not more than 51 mm, preferably not more than 31 mm, more preferably not more than 21 mm, still more preferably not more than 17 mm, especially preferably not more than 15 mm.

The zeolite mainly constituting the zeolite membrane is usually zeolite having a 6- to 12-membered oxygen ring structure, preferably zeolite having a 6- to 10-membered oxygen ring structure, more preferably zeolite having an 8-membered oxygen ring structure.

The value n of the zeolite having an n-membered oxygen ring indicates the value for the pore having the largest number of oxygen atoms among the pores forming the zeolite skeleton constituted by oxygen and T element. For example, in cases where zeolite has pores of 12-membered oxygen rings and 8-membered oxygen rings similarly to MOR-type zeolite, the zeolite is regarded as zeolite having a 12-membered oxygen ring.

Examples of zeolite having a 6- to 10-membered oxygen ring structure include AEI, AEL, AFG, ANA, BRE, CAS, CDO, CHA, DAC, DDR, DOH, EAB, EPI, ESV, EUO, FAR, FRA, FER, GIS, GIU, GOO, HEU, IMF, ITE, ITH, KFI, LEV, LIO, LOS, LTA, LTN, MAR, MEP, MER, MEL, MFI, MFS, MON, MSO, MTF, MTN, MIT, MWW, NAT, NES, NON, PAU, PHI, RHO, RRO, RTE, RTH, RUT, SGT, SOD, STF, STI, STT, TER, TOL, TON, TSC, TUN, UFI, VNI, VSV, WEI, and YUG.

In cases where the structure is larger than a 10-membered oxygen ring structure, the pore size is large. Therefore, the separation performance for organic substances with small sizes decreases, resulting in limited uses in some cases.

Among the structures of zeolite described above, AEI, CHA, KFI, LEV, LTA, PAU, RHO, RTH, or UFI is preferred. CHA, LEV, LTA, or UFI is more preferred. CHA or LTA is still more preferred. LTA is especially preferred.

The thickness of the zeolite membrane is not limited. The thickness is usually not less than 0.1 µm, preferably not less than 0.6 µm, more preferably not less than 1.0 µm, still more preferably not less than 5 µm, especially preferably not less than 7 µm. The thickness is within the range of usually not more than 100 µm, preferably not more than 60 µm, more preferably not more than 20 µm, especially preferably not more than 10 µm. In cases where the membrane thickness is too large, the permeation volume tends to be small, while in cases where the membrane thickness is too small, selectivity and membrane strength tend to be poor.

Description is given below with reference to drawings. The alcohol concentrations described in the drawings and the following description are merely examples, and not limited thereto.

(FIG. 1)

The first mode of the production method of the present invention is described below with reference to FIG. 1. In the present embodiment, a part of crude alcohol obtained by the distillation step is introduced into an adsorption-desorption column (PSA).

A water-alcohol mixture containing alcohol at not more than 20% by weight is introduced into a distillation column 1a, to obtain crude alcohol with an alcohol concentration of, for example, 94% by weight (distillation step). A part of the crude alcohol obtained is introduced into an adsorption-desorption column PSA 1b, to obtain high concentration alcohol 1 (product) containing alcohol at not less than 98% by weight. The desorbed liquid of PSA 1b is discharged from the adsorption-desorption column (adsorption-desorption step). The desorbed liquid is introduced into a dehydration apparatus B (membrane separation apparatus 1c) to separate water from alcohol, to obtain aqueous alcohol containing alcohol at not less than 94% by weight. The alcohol concentration of the aqueous alcohol is within the range of ±10% by weight, preferably within the range of ±5% by weight with respect to, more preferably the same concentration as, the concentration of the crude alcohol obtained from the distillation column.

In FIG. 1, the aqueous alcohol is introduced into a dehydration apparatus A (membrane separation apparatus 1d) together with a part of the crude alcohol obtained. By the membrane separation apparatus 1d, water is separated from alcohol to obtain high concentration alcohol 2 (product). In this mode, a membrane separation apparatus having a higher separation performance than PSA (that is, the loss in the purge side is smaller than that in PSA) is used. By this, the ratio of ethanol obtained as the product to the amount of ethanol in the crude ethanol obtained by the distillation can be effectively increased.

The high concentration alcohol 2 obtained by the membrane separation apparatus 1d is recovered as a product together with high concentration alcohol 1, so that high concentration alcohol can be produced.

(FIG. 2)

Figure 2:
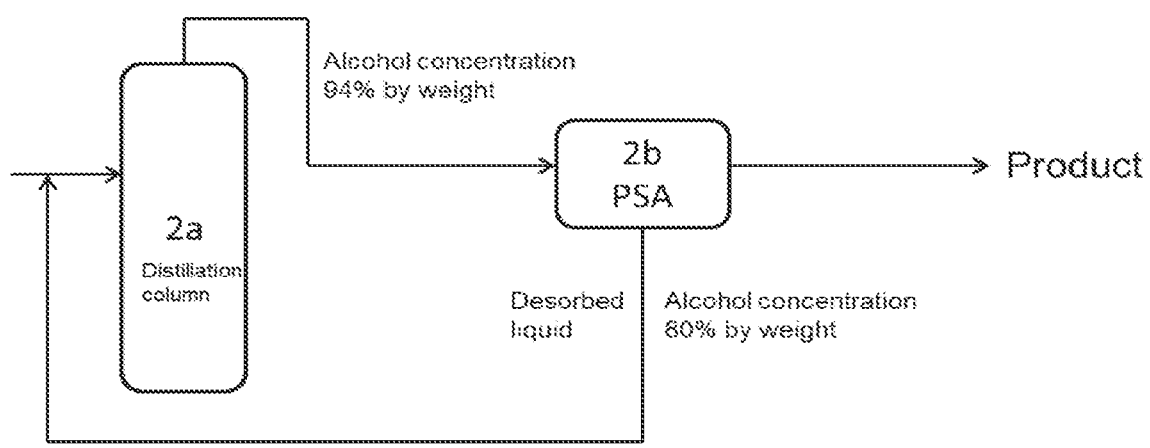
FIG. 2 is a process flow diagram showing an example of a conventional method of producing high concentration alcohol.

FIG. 2 is a specific mode corresponding to a Comparative Example. In this case, high concentration alcohol is obtained with PSA 2b alone without arranging a membrane separation apparatus. In this method, a large amount of ethanol is contained in the purge from the PSA, and the ratio of ethanol obtained as a product to the amount of ethanol in the crude ethanol obtained by the distillation is small.

(FIG. 4)

Figure 4:
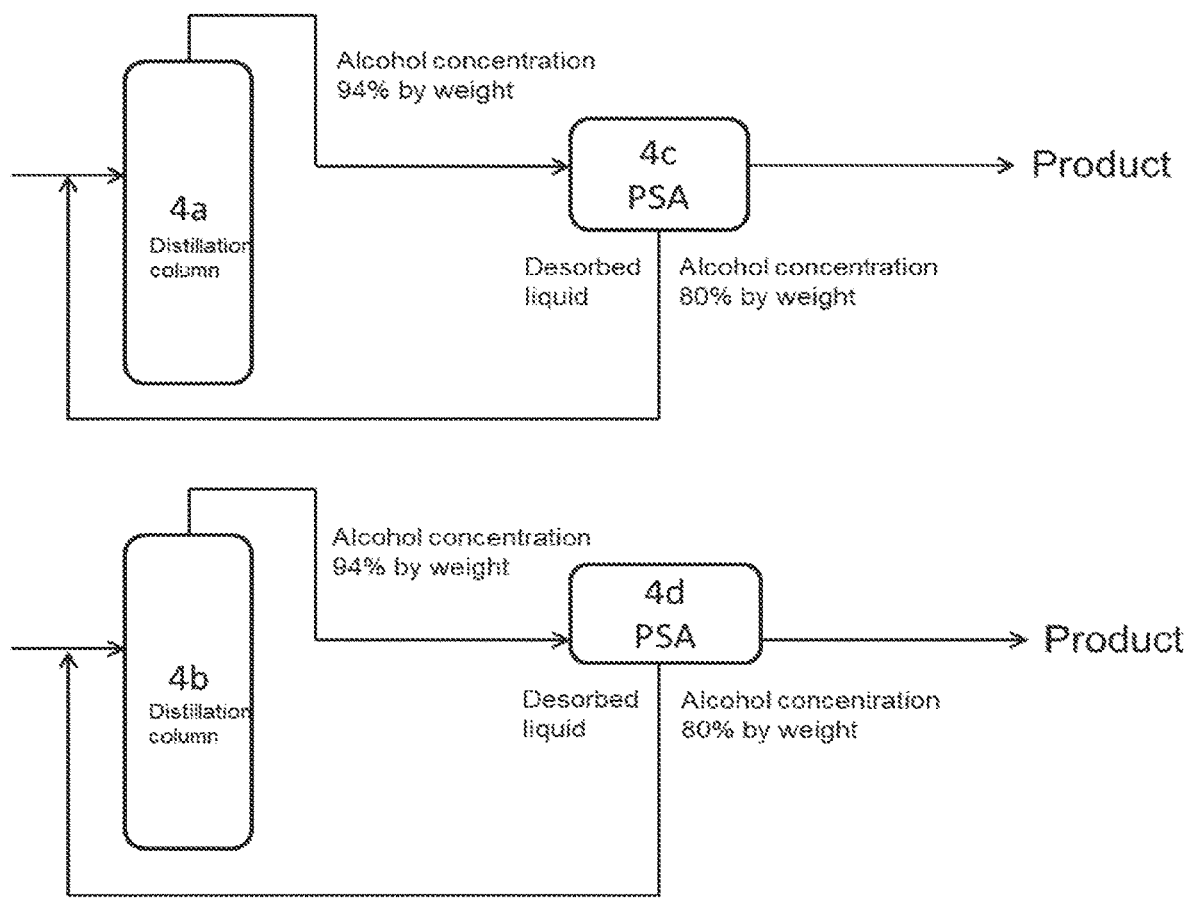
FIG. 4 is a process flow diagram showing an example of a conventional method of producing high concentration alcohol.

FIG. 4 is a specific mode corresponding to a Comparative Example. In this case, high concentration alcohol is obtained with PSA 4c or 4d alone without arranging a membrane separation apparatus. In this method, a large amount of ethanol is contained in the purge from the PSA, and the ratio of ethanol obtained as a product to the amount of ethanol in the crude ethanol obtained by the distillation is small.

(FIG. 5)

Figure 5:
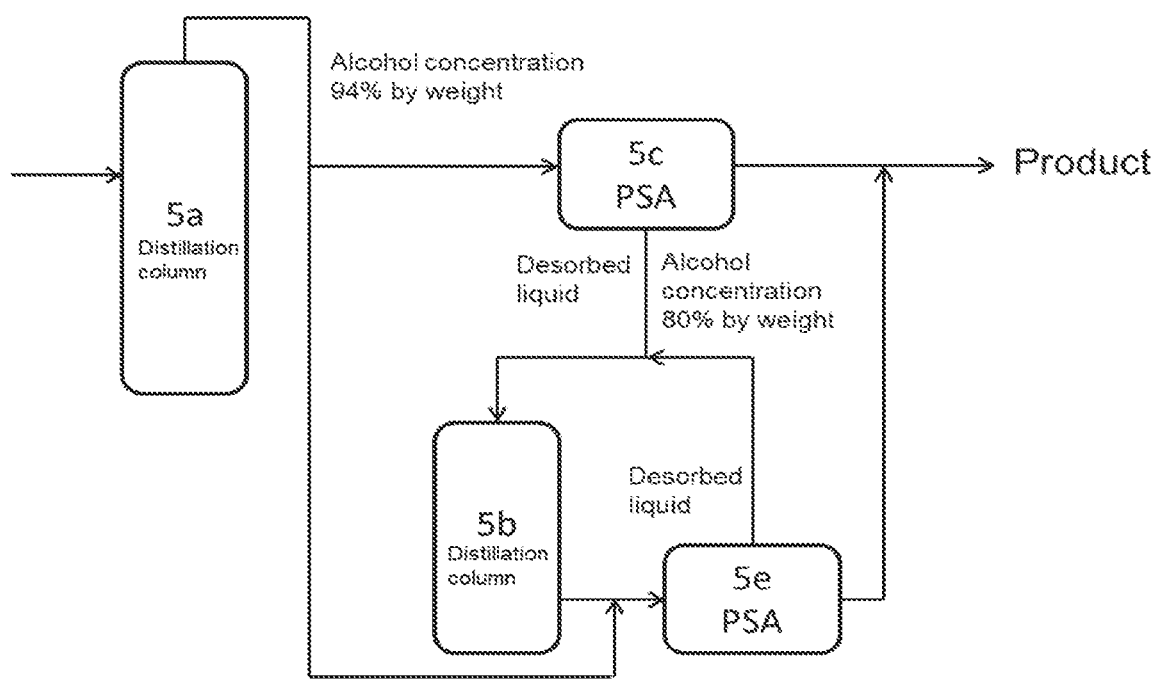
FIG. 5 is a process flow diagram showing an example of the method of producing high concentration alcohol of the present invention.

In FIG. 5, a part of crude alcohol obtained from a distillation column 5a is introduced into PSA 5c, which is an adsorption-desorption column, and the desorbed liquid discharged from the adsorption-desorption column 5c is introduced into a distillation column 5b (dehydration apparatus B). Thereafter, the aqueous alcohol obtained is introduced into PSA 5e (dehydration apparatus A), which is an adsorption-desorption column, together with crude alcohol obtained from the distillation column 5a, to obtain high concentration alcohol. The desorbed liquid discharged from PSA 5e, which is the adsorption-desorption column, may be further introduced into the distillation column 5b.

(FIG. 6)

Figure 6:
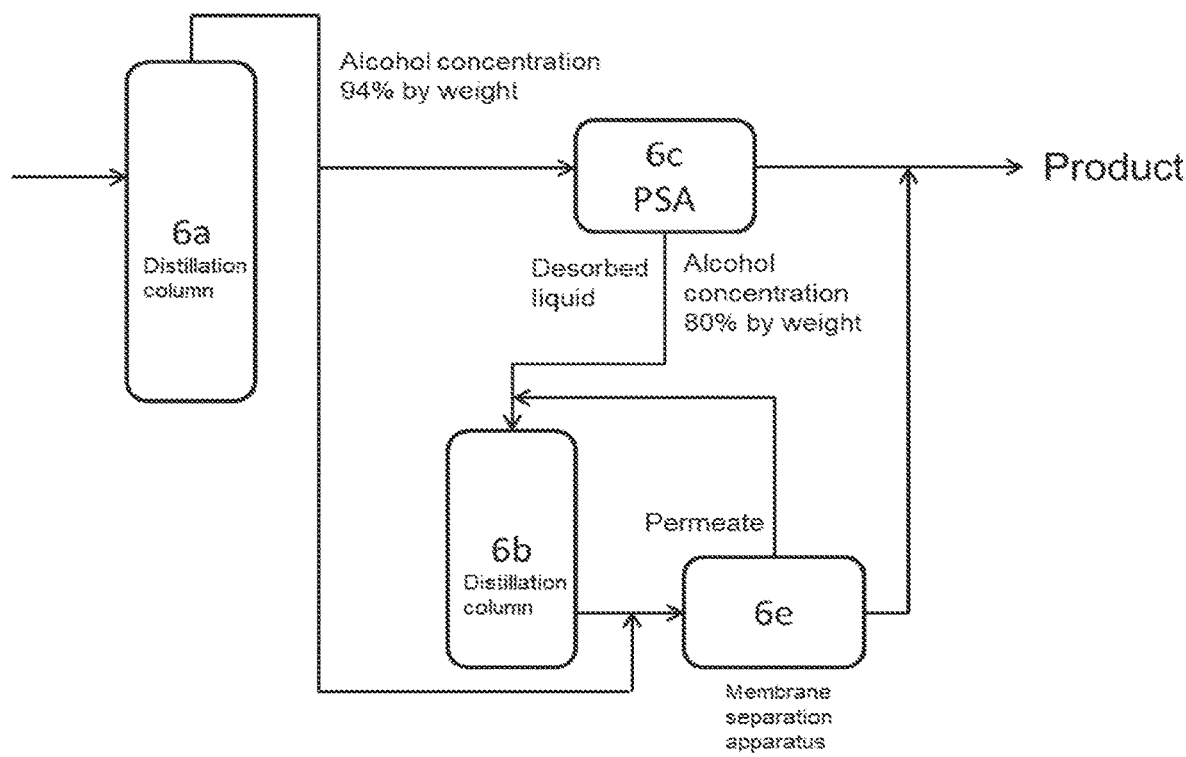
FIG. 6 is a process flow diagram showing an example of the method of producing high concentration alcohol of the present invention.

FIG. 6 shows a method in which a part of crude alcohol obtained from a distillation column 6a is introduced into PSA 6c, which is an adsorption-desorption column, and the desorbed liquid discharged from the adsorption-desorption column 6c is introduced into a distillation column 6b (dehydration apparatus B). Thereafter, the aqueous alcohol obtained is further introduced into a membrane separation apparatus 6e (dehydration apparatus A) together with crude alcohol obtained from the distillation column 6a, to obtain high concentration alcohol. The permeate obtained from the membrane separation apparatus 6e may be further introduced into the distillation column 6b.

(FIG. 7)

Figure 7:
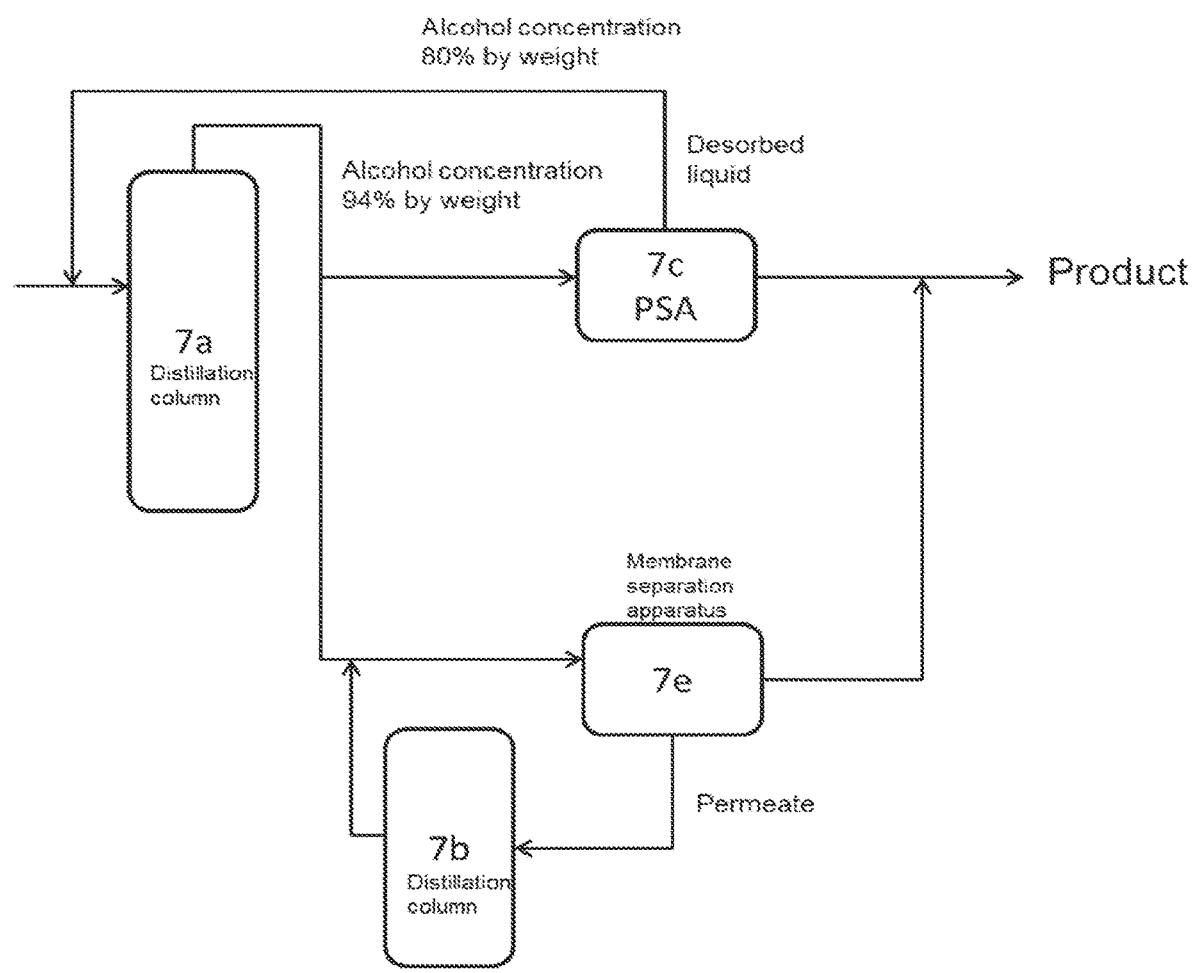
FIG. 7 is a process flow diagram showing an example of the method of producing high concentration alcohol of the present invention.

In FIG. 7, a part of crude alcohol obtained from a distillation column 7a is introduced into PSA 7c, which is an adsorption-desorption column, and the desorbed liquid discharged from the adsorption-desorption column 7c is introduced again into the distillation column 7a. On the other hand, a part of the crude alcohol obtained from the distillation column 7a is introduced into a membrane separation apparatus 7e (dehydration apparatus A), to obtain high concentration alcohol (product). The permeate obtained from the membrane separation apparatus 7e may be introduced into a distillation column 7b, and may then be introduced again into the membrane separation apparatus 7e.

(FIG. 8)

Figure 8:
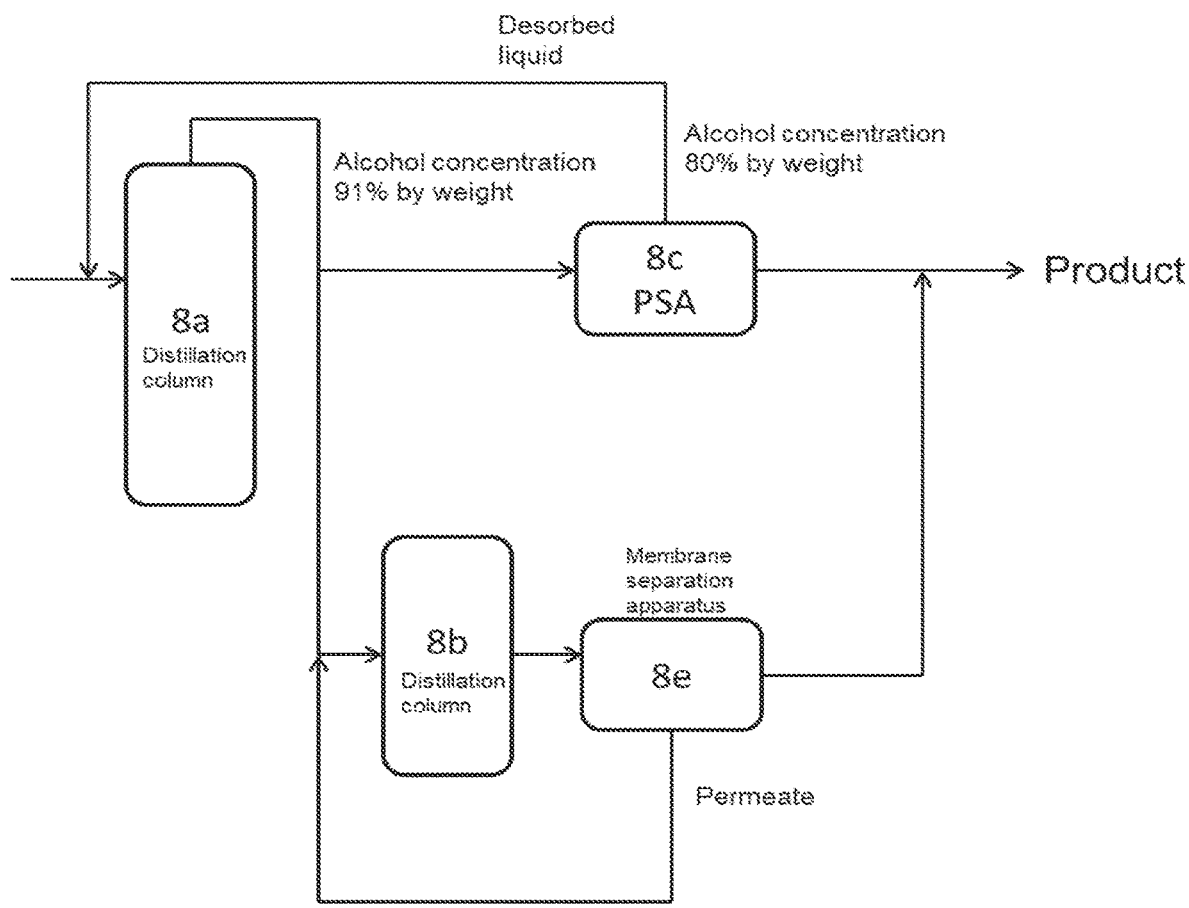
FIG. 8 is a process flow diagram showing an example of the method of producing high concentration alcohol of the present invention.

In FIG. 8, a part of crude alcohol obtained from a distillation column 8a is introduced into PSA 8c, which is an adsorption-desorption column, and the desorbed liquid discharged from the adsorption-desorption column 8c is introduced again into the distillation column 8a. A part of the crude alcohol obtained from the distillation column 8a is introduced into a distillation column 8b (dehydration apparatus A), and then the concentrated aqueous alcohol is further introduced into a membrane separation apparatus 8e, to obtain high concentration alcohol (product). The permeate obtained from the membrane separation apparatus 8e may be further introduced into the distillation column 8b.

(FIG. 9)

Figure 9:
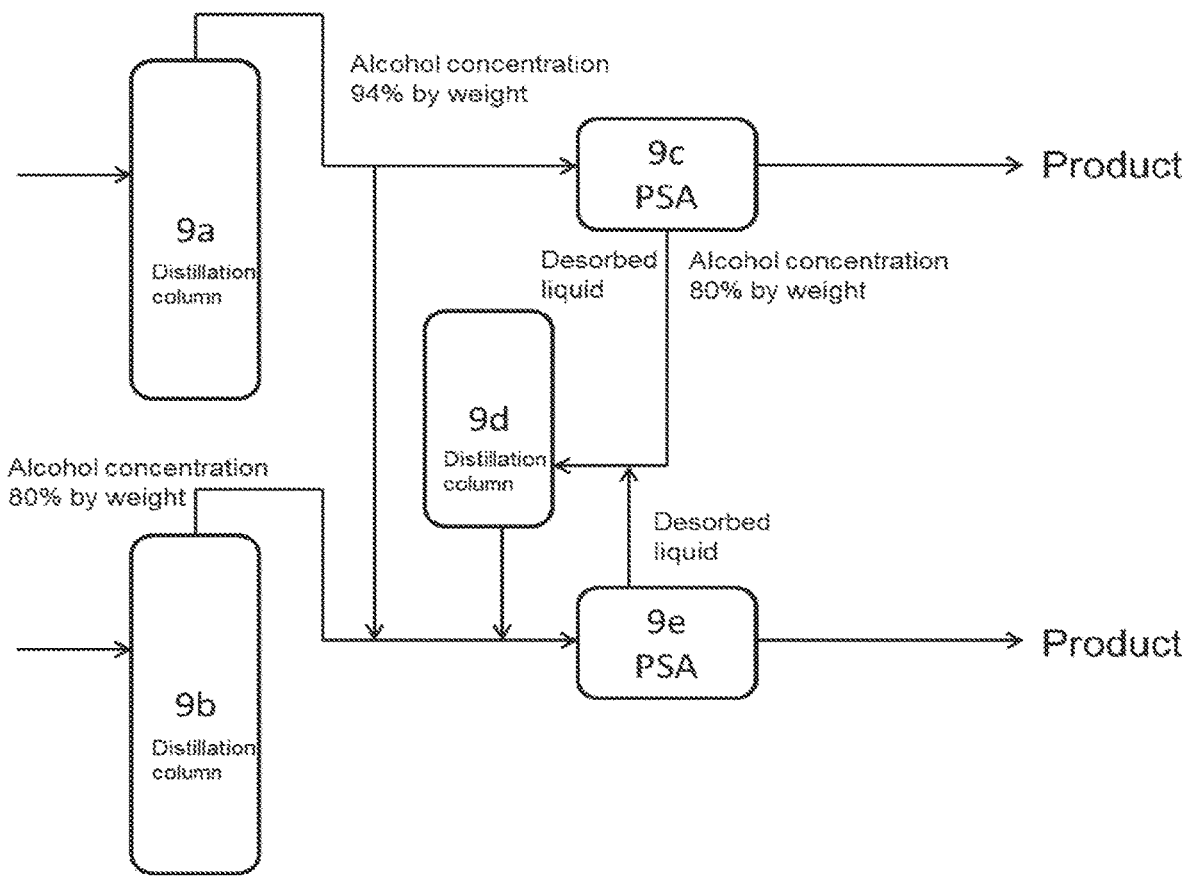
FIG. 9 is a process flow diagram showing an example of the method of producing high concentration alcohol of the present invention.

In FIG. 9, a part of crude alcohol obtained from a distillation column 9a is introduced into PSA 9c, which is an adsorption-desorption column, and the desorbed liquid discharged from the adsorption-desorption column 9c is introduced into a distillation column 9d (dehydration apparatus B). On the other hand, a part of the crude alcohol obtained from the distillation column 9a, crude alcohol obtained from a distillation column 9b, and aqueous alcohol obtained from the distillation column 9d are introduced into PSA 9e (dehydration apparatus A), which is an adsorption-desorption column, to obtain high concentration alcohol (product). The desorbed liquid obtained from the adsorption-desorption column 9e may be introduced again into the distillation column 9d.

(FIG. 10)

Figure 10:
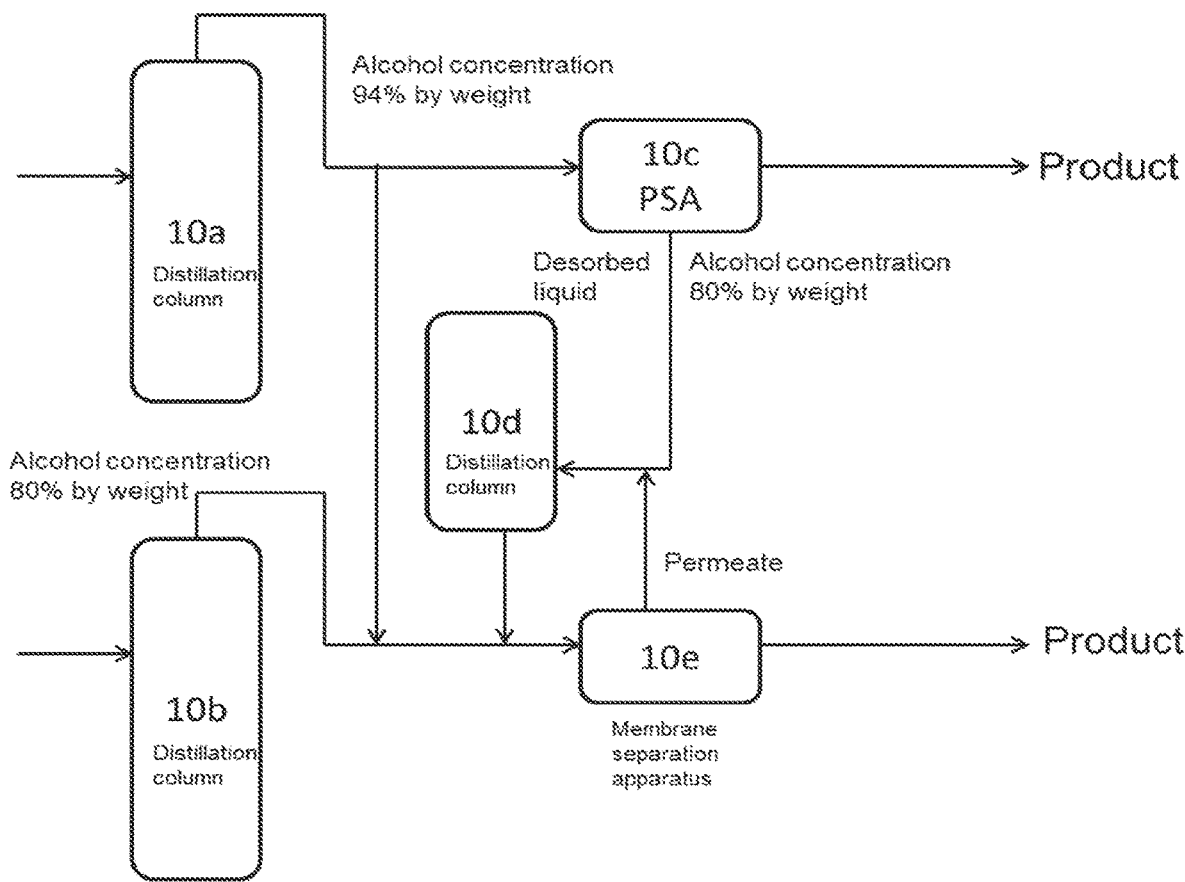
FIG. 10 is a process flow diagram showing an example of the method of producing high concentration alcohol of the present invention.

In FIG. 10, a part of crude alcohol obtained from a distillation column 10a is introduced into PSA 10c, which is an adsorption-desorption column, and the desorbed liquid discharged from the adsorption-desorption column 10c is introduced into a distillation column 10d (dehydration apparatus B). Thereafter, the aqueous alcohol obtained is introduced into a membrane separation apparatus 10e (dehydration apparatus A) together with a part of the crude alcohol obtained from the distillation column 10a and aqueous alcohol having a relatively low concentration obtained from a distillation column 10b, to obtain high concentration alcohol. The aqueous alcohol having a relatively low concentration obtained from the distillation column 10b has a concentration of 80% by weight.

(FIG. 11)

Figure 11:
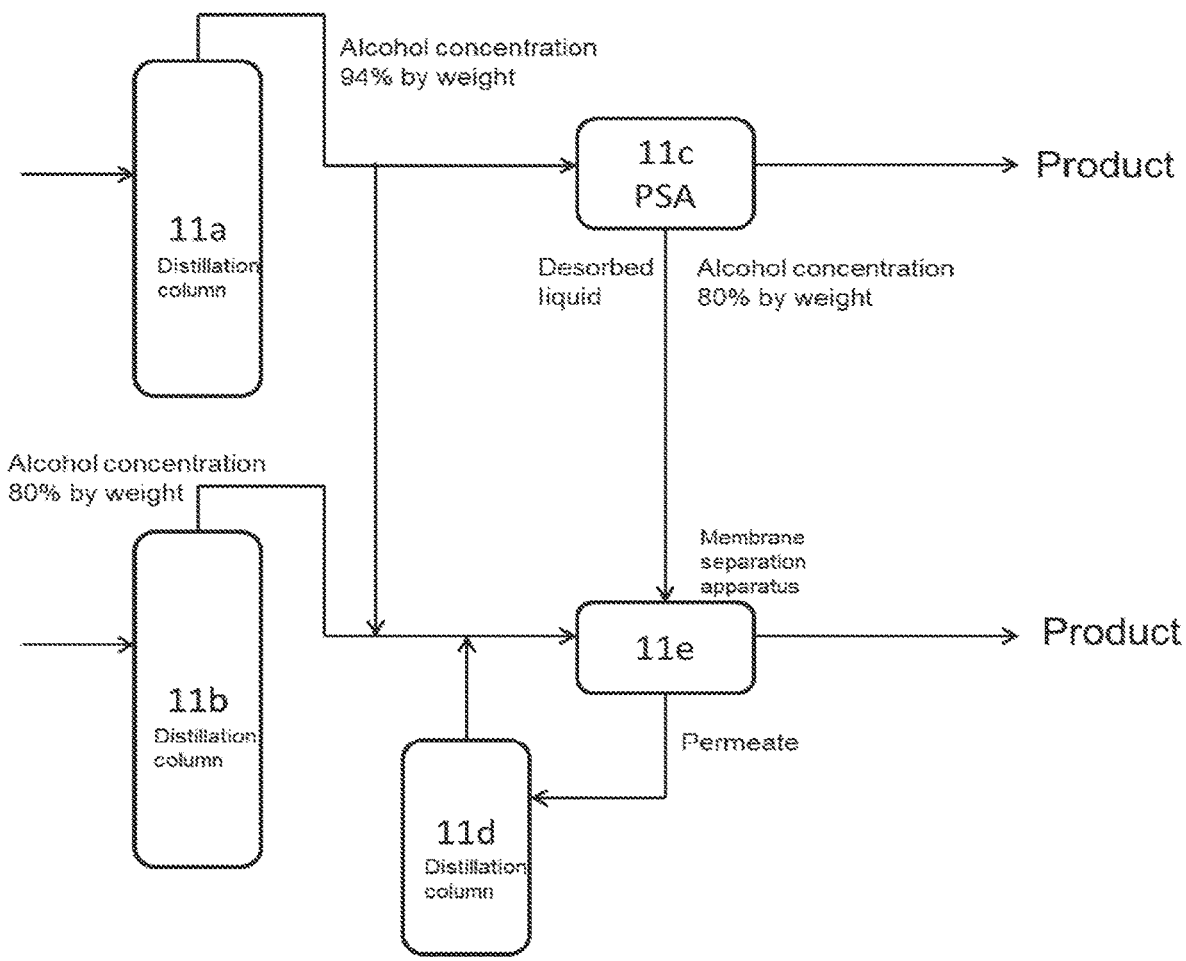
FIG. 11 is a process flow diagram showing an example of the method of producing high concentration alcohol of the present invention.

FIG. 11 is related to a case where a water-alcohol mixture is introduced into each of two distillation columns. Crude alcohol obtained from a distillation column 11a is introduced into PSA 11c, which is an adsorption-desorption column, to obtain high concentration alcohol (product). The desorbed liquid discharged from the adsorption-desorption column 11c is introduced into a membrane separation apparatus 11e (dehydration apparatus A), to obtain high concentration alcohol (product). Crude alcohol obtained from a distillation column 11b is introduced into the membrane separation apparatus 11e together with a part of crude alcohol obtained from the distillation column 11a, to obtain high concentration alcohol. The permeate obtained from the membrane separation apparatus 11e may be introduced into a distillation column 11d, and may be further introduced into the membrane separation apparatus 11e.

(FIG. 12)

Figure 12:
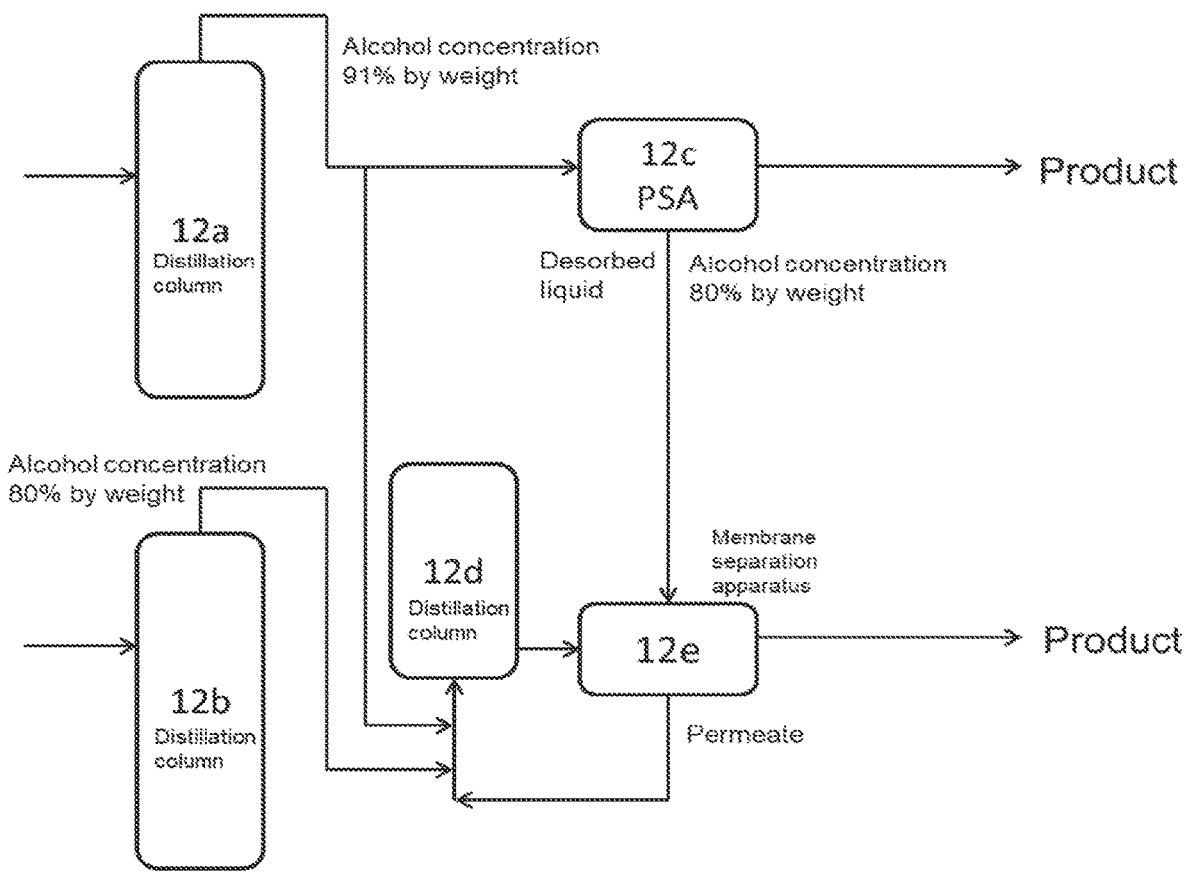
FIG. 12 is a process flow diagram showing an example of the method of producing high concentration alcohol of the present invention.

In FIG. 12, a part of crude alcohol obtained from a distillation column 12a is introduced into PSA 12c, which is an adsorption-desorption column, and the desorbed liquid discharged from the adsorption-desorption column 12c is introduced into a membrane separation apparatus 12e (dehydration apparatus A), to obtain high concentration alcohol. A part of the crude alcohol obtained from the distillation column 12a is introduced into a distillation column 12d (dehydration apparatus B) together with crude alcohol obtained from a distillation column 12b. Aqueous alcohol obtained from the distillation column 12d is introduced into the membrane separation apparatus 12e, to obtain high concentration alcohol.

(FIG. 13)

Figure 13:
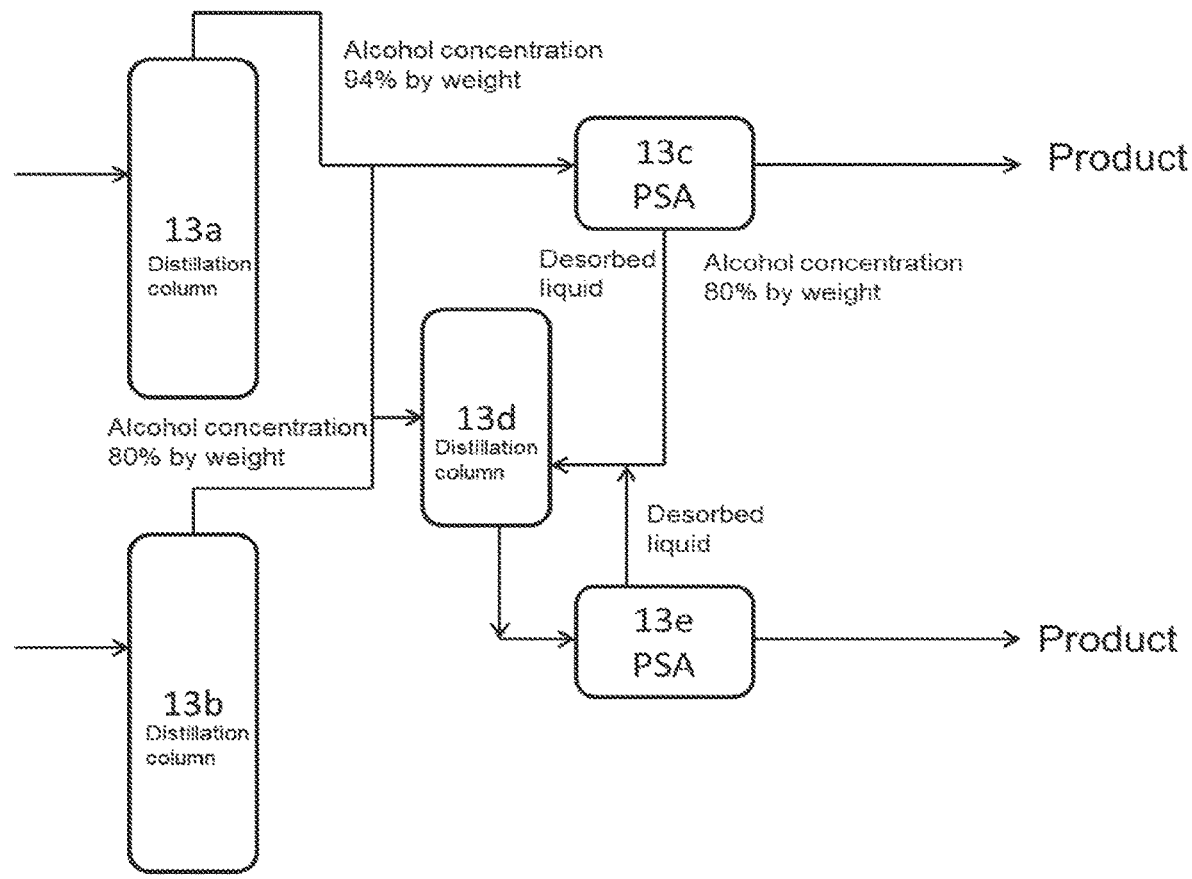
FIG. 13 is a process flow diagram showing an example of the method of producing high concentration alcohol of the present invention.

In FIG. 13, a part of crude alcohol obtained from a distillation column 13a is introduced into PSA 13c, which is an adsorption-desorption column. The desorbed liquid discharged from the adsorption-desorption column 13c is introduced into a distillation column 13d (dehydration apparatus A), and then introduced into an adsorption-desorption column 13e (dehydration apparatus B), to obtain high concentration alcohol (product). Crude alcohol obtained from a distillation column 13b may be introduced into the adsorption-desorption column 13c and/or the distillation column 13d. The desorbed liquid discharged from the adsorption-desorption column 13e may be further introduced into the distillation column 13d.

(FIG. 14)

Figure 14:
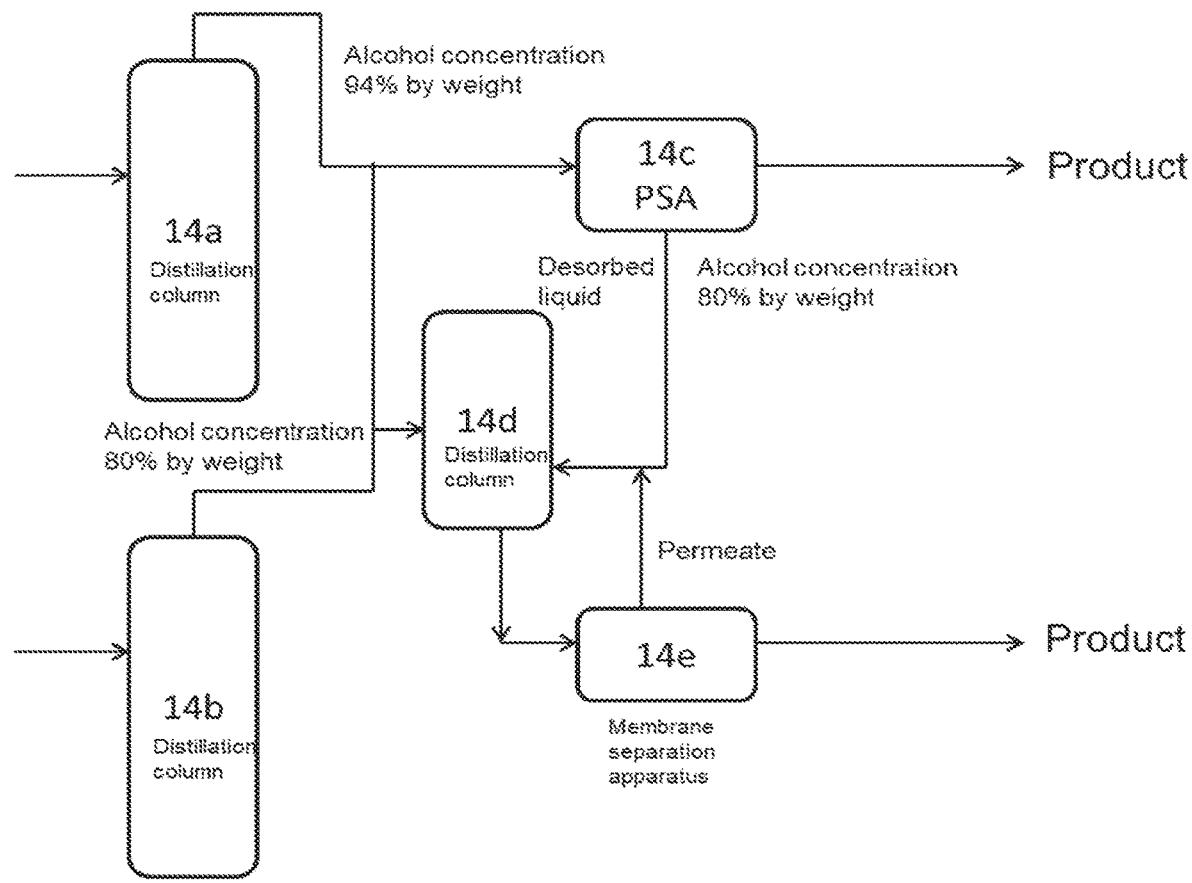
FIG. 14 is a process flow diagram showing an example of the method of producing high concentration alcohol of the present invention.

In FIG. 14, a part of crude alcohol obtained from a distillation column 14a is introduced into PSA 14c, which is an adsorption-desorption column. The desorbed liquid discharged from the adsorption-desorption column 14c is introduced into a distillation column 14d (dehydration apparatus A), and the resulting aqueous alcohol is then introduced into a membrane separation apparatus 14e (dehydration apparatus B), to obtain high concentration alcohol (product). The permeate obtained from the membrane separation apparatus 14e may be introduced into the distillation column 14d. A part of crude alcohol obtained from a distillation column 14b may be introduced into the adsorption-desorption column 14c (the introduction is not shown in the figure), and/or may be introduced into the distillation column 14d.

(FIG. 15)

Figure 15:
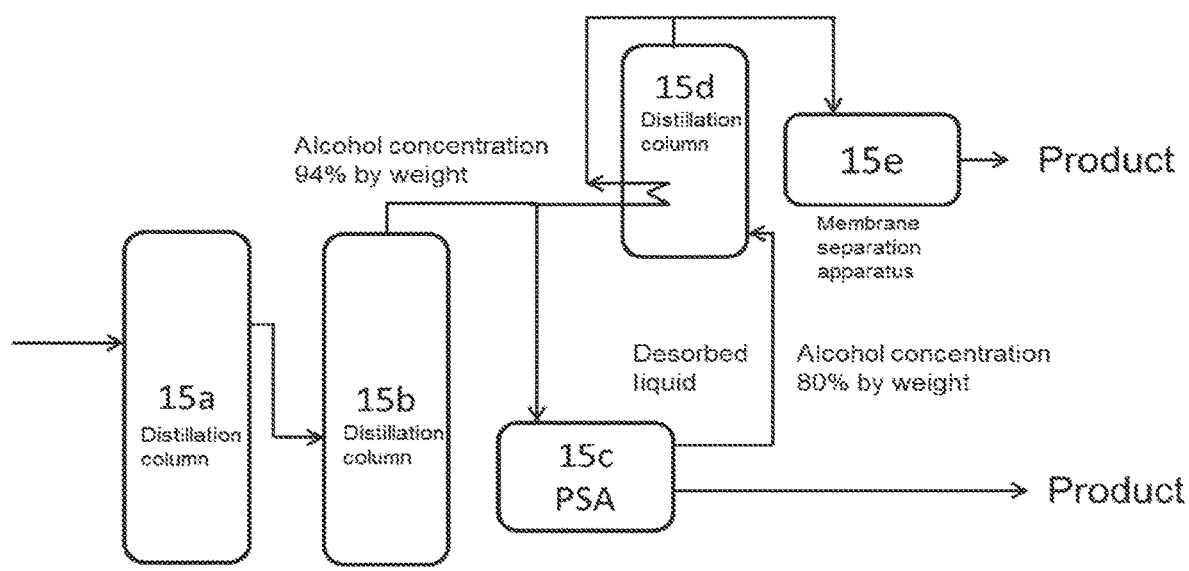
FIG. 15 is a process flow diagram showing an example of the method of producing high concentration alcohol of the present invention.

In FIG. 15, crude alcohol obtained through distillation columns 15a and 15b is introduced into each of PSA 15c, which is an adsorption-desorption column, and a distillation column 15d (dehydration apparatus A). The introduction ratio is not limited, and usually set such that a larger amount of the crude alcohol is introduced into the adsorption-desorption column 15c.

Since the crude alcohol is crude alcohol in a gaseous state obtained from the top of the distillation column 15b, its latent heat can be utilized in the distillation column 15d to provide heating means for the distillation column 15d. Aqueous alcohol obtained from the distillation column 15d is further introduced into a membrane separation apparatus 15e (dehydration apparatus B), to obtain high concentration alcohol (product) through the membrane separation apparatus 15e. The permeate obtained from the membrane separation apparatus 15e may be introduced into the distillation column 15d (the introduction is not shown in the figure).

The crude alcohol introduced into the adsorption-desorption column 15c is provided as high concentration alcohol (product) through the adsorption-desorption column 15c. The desorbed liquid discharged from the adsorption-desorption column 15c may be further introduced into the distillation column 15d.

Although two distillation columns are used in this mode, three or more distillation columns may be used. In such cases, a membrane separation apparatus(es) may be appropriately arranged depending on the processing capacity of each distillation column.

EXAMPLES

Examples are shown below for exemplification of the present invention. However, the present invention is not limited thereto.

Comparative Example 1

A water-alcohol mixture was introduced into a distillation column to obtain crude alcohol. Thereafter, the whole crude alcohol was introduced into an adsorption-desorption column. The desorbed liquid obtained from the adsorption-desorption column was introduced into a membrane separation apparatus to obtain high concentration alcohol. For this process, the total steam consumption was calculated as the energy consumption. As a result, the total steam consumption per unit energy was 1.54 (t/t).

Example 1

A water-alcohol mixture was introduced into a distillation column to obtain crude alcohol, and a part of the crude alcohol was introduced into an adsorption-desorption column, to obtain high concentration alcohol. On the other hand, a further part of the crude alcohol was introduced into a membrane separation apparatus together with the desorbed liquid from the adsorption-desorption column. The total steam consumption in this case was calculated. As a result, the total steam consumption per unit energy was 1.45 (t/t).

Example 2

The same process as in Example 1 was carried out except that the desorbed liquid from the adsorption-desorption column was introduced into a stripper, followed by introduction into the membrane separation apparatus together with a further part of the crude alcohol. The total steam consumption in this case was calculated. As a result, the total steam consumption per unit energy was 1.23 (t/t).

The present invention also includes the following mode (A).

The present invention relates to (A) a method of producing high concentration alcohol by dehydration of a water-alcohol mixture, including:

a distillation step of introducing a water-alcohol mixture into a distillation column to obtain crude alcohol; and an adsorption-desorption step of introducing the resulting crude alcohol into an adsorption-desorption column to obtain high concentration alcohol 1;

wherein a desorbed liquid discharged from the adsorption-desorption column in the adsorption-desorption step is introduced into a dehydration apparatus 1, and aqueous alcohol obtained from the dehydration apparatus 1 is further introduced into a dehydration apparatus 2, which is a further dehydration apparatus, to obtain high concentration alcohol 2.

In particular, the method of producing high concentration alcohol according to mode (A) is a method of producing high concentration alcohol containing alcohol at not less than 98% by weight by dehydration of a water-alcohol mixture containing alcohol at not more than 20% by weight, which method includes:

a distillation step of introducing a water-alcohol mixture containing alcohol at not more than 20% by weight into a distillation column to obtain crude alcohol containing alcohol at not less than 30% by weight;

an adsorption-desorption step of introducing the resulting crude alcohol into an adsorption-desorption column to obtain high concentration alcohol 1 containing alcohol at not less than 98% by weight;

a membrane separation step 1 of introducing a desorbed liquid containing alcohol at not more than 94% by weight discharged from the adsorption-desorption column in the adsorption-desorption step into a membrane separation apparatus 1 to separate water from alcohol, to obtain aqueous alcohol containing alcohol at not less than 98% by weight; and a membrane separation step 2 of introducing the aqueous alcohol obtained in the membrane separation step 1 and a part of the crude alcohol obtained by the distillation step into a membrane separation apparatus 2 to separate water from alcohol, to further obtain high concentration alcohol 2 at not less than 98% by weight.

Figure 3:
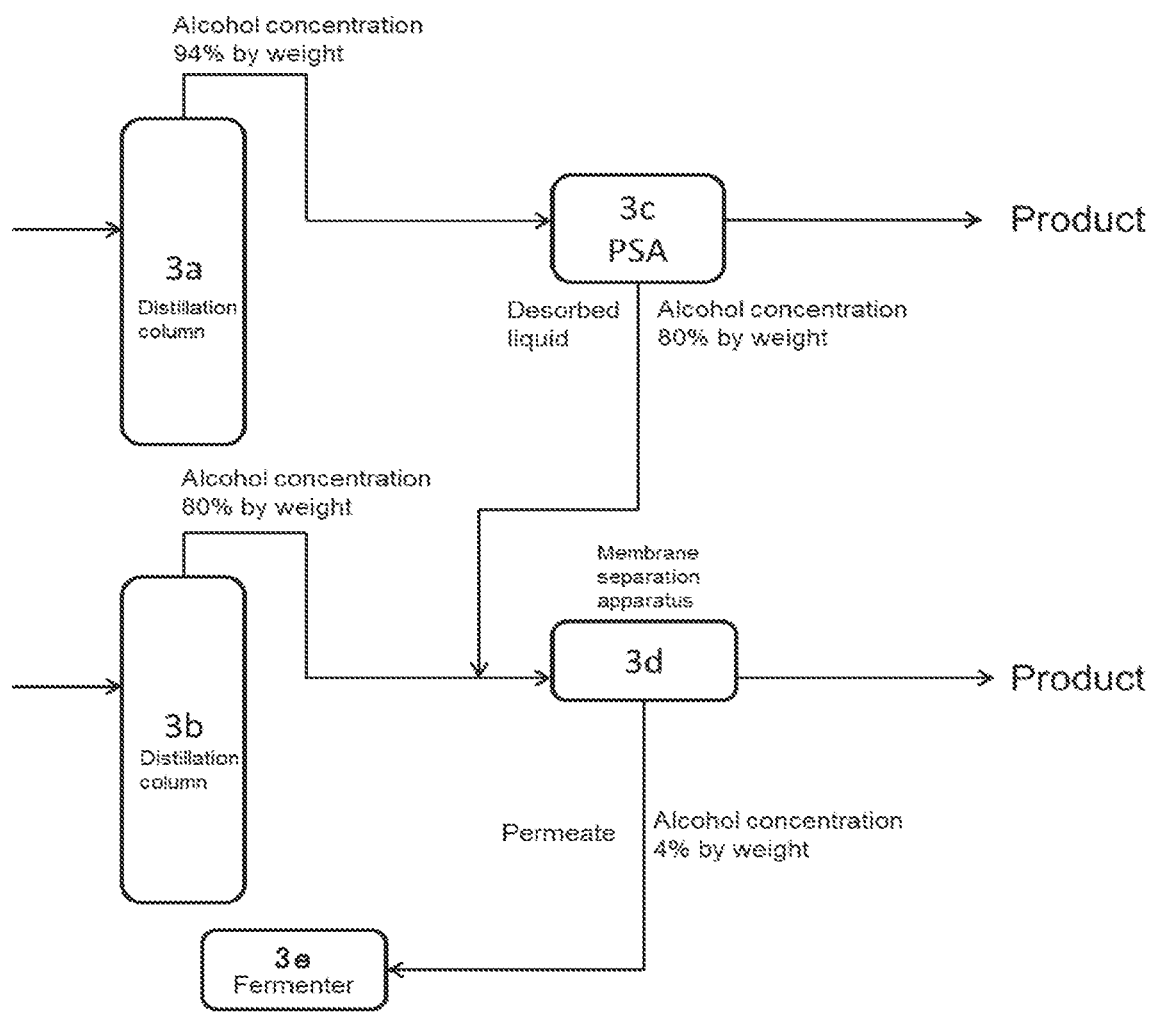
FIG. 3 is a process flow diagram showing an example of the method of producing high concentration alcohol in another mode of the present invention.

As another mode, the present invention also includes mode (B). Its specific mode is shown in FIG. 3. The present invention relates to (B) a method of producing high concentration alcohol by dehydration of a water-alcohol mixture, including:

a distillation step of introducing a water-alcohol mixture into two or more distillation columns to obtain crude alcohol from each distillation column;

an adsorption-desorption step of introducing crude alcohol 1 obtained from at least one distillation column (distillation column 1) into an adsorption-desorption column to obtain high concentration alcohol 1; and a membrane separation step of introducing a desorbed liquid discharged from the adsorption-desorption column in the adsorption-desorption step into a membrane separation apparatus to obtain high concentration alcohol 2;

wherein (a) crude alcohol 2 obtained from a further distillation column (distillation column 2) is introduced into the membrane separation apparatus; or (b) crude alcohol 2 obtained from a further distillation column (distillation column 2) is introduced into a dehydration apparatus to obtain aqueous alcohol, and the aqueous alcohol is then introduced into the membrane separation apparatus; to obtain high concentration alcohol 2.

In particular, the method of producing high concentration alcohol according to mode (B) is a method of producing high concentration alcohol containing alcohol at not less than 98% by weight by dehydration of a water-alcohol mixture containing alcohol at not more than 20% by weight, which method includes:

a distillation step of introducing a water-alcohol mixture containing alcohol at not more than 20% by weight into two or more distillation columns to obtain crude alcohol containing alcohol at not less than 30% by weight from each distillation column;

an adsorption-desorption step of introducing crude alcohol 1 obtained from at least one distillation column (distillation column 1) into an adsorption-desorption column to obtain high concentration alcohol 1 containing alcohol at not less than 98% by weight; and a membrane separation step 3 of introducing crude alcohol 2 containing alcohol at not less than 30% by weight obtained from a further distillation column (distillation column 2), and a desorbed liquid containing alcohol at not more than 94% by weight discharged from the adsorption-desorption column in the adsorption-desorption step, into a membrane separation apparatus to separate water from alcohol, to obtain high concentration alcohol 2 at not less than 98% by weight.

Although the present invention has been described with reference to specific embodiments, each embodiment was presented as an example and does not limit the scope of the present invention. Each of the embodiments described herein can be variously modified without departing from the spirit of the invention, and can be combined with characteristics described by other embodiments so long as it can be enabled.

What is claimed is:

1. A method of producing high concentration alcohol by dehydration of a water-alcohol mixture, the method comprising:

distilling a water-alcohol mixture in a distillation column to obtain a first crude alcohol;

adsorbing and desorbing a first part of the first crude alcohol in an adsorption-desorption column to obtain a first high concentration alcohol, as a part of the high concentration alcohol, and a desorbed liquid; and dehydrating the desorbed liquid, mixed with a second part of the first crude alcohol, in a first dehydration apparatus to obtain a second high concentration alcohol, as a part of the high concentration alcohol, wherein the high concentration alcohol has a higher alcohol concentration than the water-alcohol mixture and the crude alcohol.

2. The method of claim 1, wherein the first dehydration apparatus is a first membrane separation apparatus.

3. The method of claim 1, further comprising:

introducing the desorbed liquid into a second dehydration apparatus to increase the alcohol concentration of the desorbed liquid, and obtain an increased alcohol portion;

mixing the increased alcohol portion with the first part of the first crude alcohol, to obtain a combined stream; and introducing the combined stream into the first dehydration apparatus.

4. The method of claim 3, further comprising:

introducing a permeate from the first dehydration apparatus into the second dehydration apparatus.

5. The method of claim 1, further comprising:

combining a second crude alcohol from a further distillation column with the second part of the second crude alcohol, is introduced into the first dehydration apparatus.

6. The method of claim 1, wherein the water-alcohol mixture is a mixture obtained by alcohol fermentation in a fermenter.

7. The method of claim 1, wherein the crude alcohol obtained in the distillation step has an alcohol concentration of not less than 50 wt. %.

8. The method of claim 1, wherein the crude alcohol obtained in the distillation step has an alcohol concentration of not more than 95 wt. %.

9. The method of claim 1, wherein the first high concentration alcohol has an alcohol concentration of not less than 98 wt. %.

10. The method of claim 1, wherein the desorbed liquid has an alcohol concentration in a range of from 30 to 80 wt. %.

11. The method of claim 1, wherein an amount in a range of from 10 to 40 wt. % of the crude alcohol obtained by the distilling is mixed with the desorbed liquid and introduced into the first dehydration apparatus.

12. The method of claim 1, wherein the second high concentration alcohol has an alcohol concentration of not less than 98 wt. %.

13. The method of claim 1, wherein a mixture comprising the desorbed liquid and the first part of the first crude alcohol, introduced into the first dehydration apparatus, has an alcohol concentration of not less than 50 wt. %.

14. The method of claim 1, wherein a mixture comprising the desorbed liquid and the first part of the first crude alcohol, introduced into the first dehydration apparatus, has an alcohol concentration of not more than 94 wt. %.

15. The method of claim 3, wherein the increased alcohol portion has an alcohol concentration of not less than 40 wt. %.

16. The method of claim 1, wherein the desorbed liquid has an alcohol concentration within ±40 wt. % of an alcohol concentration of the first crude alcohol.

17. The method of claim 3, wherein the increased alcohol portion has an alcohol concentration of within ±40 wt. % of an alcohol concentration of the first crude alcohol.

18. The method of claim 1, wherein the first dehydration apparatus is a first membrane separation apparatus.

19. The method of claim 3, wherein the second dehydration apparatus is a first membrane separation apparatus.

* * * * *